United States Patent
Nakane

(10) Patent No.: US 6,750,038 B1
(45) Date of Patent: Jun. 15, 2004

(54) RAPID ANTIBIOTIC SUSCEPTIBILITY TEST

(75) Inventor: Paul K. Nakane, Mountain View, CA (US)

(73) Assignee: Essential Therapeutics, Inc., Waltham, MA (US)

( * ) Notice: Subject to any disclaimer, the term of this patent is extended or adjusted under 35 U.S.C. 154(b) by 0 days.

(21) Appl. No.: 09/920,785

(22) Filed: Aug. 1, 2001

Related U.S. Application Data

(60) Provisional application No. 60/236,901, filed on Sep. 28, 2000.

(51) Int. Cl.[7] ................................................. C12Q 1/18
(52) U.S. Cl. ........................................................... 435/32
(58) Field of Search ............................................ 435/32

(56) References Cited

U.S. PATENT DOCUMENTS 4,622,297 A * 11/1986 Kappner et al. .............. 435/32
5,336,600 A * 8/1994 Monget ........................ 435/34
5,843,699 A * 12/1998 Strenkoski et al. ........... 435/34
5,998,159 A * 12/1999 Watson et al. ................ 435/32

FOREIGN PATENT DOCUMENTS

WO          9918232       *  4/1999

OTHER PUBLICATIONS

SIGMA CATALOGUE 1997 p. 97 A6670 Amethopterin.*

Chem ABS Registry NADP 53–59–8/RN 2003.*

* cited by examiner

*Primary Examiner*—Herbert J. Lilling
(74) *Attorney, Agent, or Firm*—Bernard F. Rose; Bingham McCutchen LLP

(57) ABSTRACT

This invention relates to a method for the rapidly determining the susceptibility of bacteria to antibiotics using histochemical detection of enzyme inhibition by the antibiotic.

18 Claims, No Drawings

RAPID ANTIBIOTIC SUSCEPTIBILITY TEST

RELATED APPLICATIONS

This application is based on and claims priority from Provisional Patent Application Ser. No. 60/236,901, which was filed Sep. 28, 2000, and which is incorporated by reference as if fully set forth herein.

BACKGROUND OF THE INVENTION

The following is offered as background information only and is not admitted to be prior art to the present invention.

The arsenal of drugs available to physicians for the treatment of infection is rapidly diminishing because potent classes of antibiotics such as the beta-lactams, macrolides, quinolones, tetracyclines and aminoglycosides, are falling victim to the phenomenon of bacterial resistance. For example, in a 1995 study, Fish, et al., reviewed 173 studies encompassing over 14,0000 patients, eight antibiotic classes and 225 individual treatment regimes (*Pharmacotherapy*, 1995, 15(3):279–291). They found resistance reported in 4% of all organisms and 5.6% of all infections treated. Furthermore, the appearance of cross-resistance, the ability of a bacterial strain resistant to one antibiotic to resist one or more other, even structurally different, antibiotics, is also increasing. Bacterial cells can acquire antibiotic resistance in several ways. One of these is simply by natural selection. Within a group of bacteria of the same species there often will be found individual members which have one or more altered genes that confer resistance to a particular antibiotic. These altered genes may arise as the result of natural mutations or by assimilation of genes from other already resistant bacteria through such processes as conjugation.

When a species of bacteria is challenged by an antibiotic, susceptible members die while those which are resistant, survive, reproduce and pass on their resistance. The more antibiotics bacteria is exposed to, the greater the probability that they will develop general resistance to antibiotics. Thus, the indiscriminate use of antibiotics can act as an effective screening mechanism for bacteria leading eventually to extremely resistant strains. However, the clinician faced with an unknown infection in a patient often has no choice. Speed in initiating treatment is often crucial to the well-being of the patient so the clinician must often make an educated guess as to what treatment regime to try while he or she awaits identification of the actual causal organism, at which time a more directed treatment regime can be initiated. The initial treatment selected, of necessity, usually involves use of the broadest-spectrum, most potent antibiotics available, which, unfortunately is the perfect recipe for the development of super-resistant bacterial strains by the selection process discussed above.

Resistance is already well-established among several clinically important bacteria and is quickly limiting the utility of the most commonly prescribed antibiotics. In particular, resistant strains of Pseudomonas, Eschericia, Streptococcus, Staphlococcus, Enterococcus, Enterobacteriaceae, Mycobacteria, Klebsiella and Haemophilis have arisen and are threatening a host of otherwise successful antibiotic therapy strategies.

One way to combat the emergence of resistance is to determine as rapidly as possible the antibiotic susceptibility of a particular infection-causing bacteria. Not only is this important to the well-being of the patient, it will assist in the control of the proliferation of antibiotic resistance among bacteria strains by selective, targeted application of antibiotic treatment. The techniques presently available and in widest use, however, do not provide a sufficiently rapid method for such determination.

A standard approach to determining the most appropriate antibiotic treatment strategy is to first identify the causal bacteria species so that an antibiotic known to be effective against that species can be prescribed. This involves isolation of bacterial cells, increasing their numbers by growing them in a culture medium and then identifying the species (and possibly the strain) by their genetic characteristics, morphology, staining pattern, etc. The culturing approach has the advantage of creating a large number of intact microorganisms which allows relatively easy identification. However, the technique suffers from that fact that it often takes a substantial amount of time to, first, grow enough of the bacteria to identify, and, second, to actually evaluate the spectrum of physiological properties necessary to make a positive identification. In the meantime, the patient may be subjected to broad-spectrum drug treatment, which not only may not be entirely effective but, as discussed above, may exacerbate the emergence of resistant strains. Furthermore, even though the species of the infecting organism is identified, it may be a resistant strain which cannot be treated with a conventional antibiotic but, rather, may require a more specific treatment regime. Unfortunately, this is difficult to accomplish since any such specific regime will depend greatly on the nature of the target bacteria. Thus, it would be desirable to be able to determine the exact susceptibility of the actual infecting bacteria prior to initiating treatment.

U.S. Pat. No. 5,989,853, to Bochner, et al. (issued Nov. 23, 1999), purports to disclose a rapid means of microorganism identification. The procedure involves a multi-test format in which the organisms are suspended in a gel matrix containing an indicator and test substances such as carbon sources and anti-microbial agents. Carbon sources are selected that can differentiate between bacteria, that is, sources which are used by some bacteria and not others. Anti-microbial agents are similarly selected; i.e., the ones selected are specific for certain bacterial species thereby making them also useful for differentiating among species. This procedure, however, requires traditional culturing to obtain a sufficient population of bacteria for the procedure.

Johnson, et al., U.S. Pat. No. 6,043,048, issued Mar. 28, 2000, describe a method for the specific determination of beta-lactam antibiotic susceptibility in a target bacterial strain. The bacteria strain is placed on growth media in the presence of both an antibiotic which induces the production of β-lactam-detoxifying enzymes (a β-lactamase) and a beta-lactam indicator antibiotic (which kills or inhibits the growth of bacteria not capable of producing a β-lactamase. An essential-nutrient-containing fluorogenic compound is also added to the growth medium. A susceptible bacterial strain, that is, one which cannot be induced to produce beta-lactamase, will metabolize the nutrient-containing compound and will not cause the release the fluorogenic agent. Thus, in a culture of susceptible bacteria, no increase in fluorescence will be observed. Resistant bacteria, on the other hand, will metabolize the nutrient/fluorphor compound, resulting in increased fluorescence. This procedure has limited utility in that it only provides susceptibility/resistance information for those bacteria that rely on β-lactamases as the basis for their resistant.

Another disclosure, U.S. Pat. No. 5,925,884 to Robinson et al. (issued Jul. 20, 1999), describes an automated system for analyzing a bacterial infection for both identification of the causal agent and determination of antibiotic susceptibility. A sample of material to be analyzed is placed in a test card which has been pre-loaded with either bacterial strain specific growth media or various concentrations of different antibiotics. The cards are incubated and, at intervals, read in a transmittance analyzer (for identification by turbidity) or a fluorescence analyzer (for antibiotic susceptibility by release of a fluorophore). The patent indicates that results should be obtainable in from 2 to 18 hours depending on the incubation time required for the bacterial. However, independent literature indicates that the time is more in the range of 4 to 16 hours.

A procedure for identifying bacteria and determining minimum inhibitory concentrations (MIC) values of antimicrobial agents is disclosed in U.S. Pat. No. 4,448,534 to Wertz ( May 15, 1984). This procedure basically involves an instrumental procedure for analyzing growth in culture. That is, bacteria that can grow in the medium will cause higher turbidity readings than those that can't. According to the patentees, use of optical methods permits earlier and more accurate turbidity measurement and therefore faster and more accurate determinations of MICs. However, the procedure is nonetheless dependent on the growth of the bacteria in a growth medium, which, as noted previously, is the time-consuming aspect of most susceptibility tests.

Using the above and other similar techniques, a number of instruments have been introduced to automate antibiotic susceptibility detection. For example, the Aladin and Uniscept instruments of Automated Laboratory Diagnostics and the AutoSceptor of Becton Dickinson are purportedly able to determine antibiotic susceptibility in 18–24 hours, the Vitek instrument by bioMerieux is stated to provide antibiotic susceptibility in from 2 to 8 hours (although independent literature sources indicate that the required time is more in the range of 4 to 16 hours), the Sensititre® by Radiometer America is claimed to be able to determine susceptibility in 5–8 hours and the Walkaway 96®, Walkaway-40®, and Autoscan-4® of Baxter Diagnostics are said to be able to determine susceptibility in from 3.5 to 7 hours.

What is needed is a method for unequivocally and accurately determining the susceptibility of an unknown bacteria to an antibiotic in the first hour to a maximum of two hours after a patient has been admitted for treatment, that is, a method which operates without the necessity of lengthy incubation times.

SUMMARY OF THE INVENTION

The present invention meets the above need by providing a rapid means of determining the susceptibility of bacterial cells to antibiotics based on the histochemical detection of the response of the cells to the antibiotic.

Thus, in one aspect, the present invention relates to a method for determining susceptibility of bacterial cells to an antibiotic comprising: providing a test substance containing bacterial cells; contacting the test substance with a growth medium containing an antibiotic, known to inhibit an operative enzyme of a bacterial biochemical pathway, to form a test substrate; incubating the test substrate; adding to the test substrate a histochemical reagent capable of generating a chromogenic compound as the result of interaction with the biochemical pathway, if the operative enzyme is not inhibited by the antibiotic; and, observing the bacterial cells in the test substrate for the presence of the chromogenic compound.

In another aspect this invention relates to the above method further comprising:
contacting an aliquot of the test substance containing the bacterial cells with growth medium not containing the antibiotic to form a control substrate; incubating the control substrate;
adding the histochemical reagent to the control substrate; and, observing the bacterial cells in the control substrate for the presence of the chromogenic compound.
Optionally, the bacterial cells may be fixed, as defined elsewhere herein, at any appropriate stage in the testing sequence, such appropriate stages being readily discernable to those skilled in the art based on the disclosures herein.

In yet another aspect, this invention relates to the above method in which the bacterial cells are selected from the group consisting of Pseudomonas, Eschericia, Streptococcus, Staphlococcus, Enterococcus, Enterobacteriaceae, Mycobacteria, Klebsiella and Haemophilis.

In still another aspect, this invention relates to the above method in which the operative enzyme is selected from the group consisting of transpeptidase, carboxypeptidase, tetrahydropteroic acid synthetase and dihydrofolate reductase.

In a further aspect, this invention relates to the above method in which the antibiotic is selected from the group consisting of a β-lactam, a tetracycline, an aminoglycoside, a sulfonamide, a macrolide, a fluoroquinolone and trimethoprim antibiotic. In particular, the antibiotic is selected from the group consisting of ampicillin, cefazolin, cephalothin, ceftazidime, gentamycin, mezlocillin, oxacillin, penicillin, piperacillin, ticarcillin and trimethoprim.

It is also an aspect of this invention that, in the above method, the test substrate, and the control substrate if used, are incubated from about 1 to about 120 minutes.

The test substrate, and the control substrate if used, are incubated from about 30 to about 90 minutes in another aspect of this invention.

In a presently preferred embodiment of this invention, the test substrate, and the control substrate if used, are incubated from about 10 to about 40 minutes.

It is an aspect of this invention that the test substance comprises a body fluid.

The body fluid is selected from the group consisting of serum, plasma, phlegm, saliva, spinal fluid, nasal discharge, ocular discharge and pus in still another aspect of this invention.

It is also an aspect of this invention that the test substance is selected from group consisting of tissue and feces.

The chromogenic compound is one that is observable by the naked eye or through instrumental means, such as, without limitation, a light microscope.

In a further aspect of this invention, the antibiotic is methoprim.

When the antibiotic is methoprim, the enzyme-catalyzed biochemical pathway is a folic acid synthesis pathway in a still further aspect of this invention.

When the antibiotic is methoprim, the test substrate is washed with pH6 phosphate buffer prior to contact with the histochemical reagent in an aspect of this invention.

When the antibiotic is methoprim, the histochemical reagent comprises TNBT (tetranitro blue tetrazolium), magnesium chloride, sodium azide, nicotinamide, ADENINE diphosphate (NADP) and dihydrofolic acid in another aspect of this invention.

An aspect of this invention is a kit for determining the susceptibility of a bacterial cells to one or more antibiotics comprising one or more histochemical reagent(s), each of which is capable of generating a chromogenic compound by interacting with a bacterial biochemical pathway if an operative enzyme of that pathway is not inhibited by an antibiotic.

Another aspect is this invention is the above kit, further comprising one or more antibiotic(s) that are known to inhibit the activity of an operative enzyme of a bacterial biochemical pathway that one or more of the histochemical reagent(s) is capable of interacting with to form a chromogenic compound if the operative enzyme is not inhibited by the antibiotic.

The above kit further comprises a growth medium in an aspect of this invention.

The above kit further comprises a fixing agent in another aspect of this invention.

An aspect of this invention is a method for determining the susceptibility of bacterial cells to a plurality of antibiotics, comprising:

providing a test substance containing bacterial cells;

providing a test plate having a plurality of wells, each well comprising a growth medium and a different antibiotic, wherein each antibiotic is known to inhibit an operative enzyme of a bacterial biochemical pathway;

placing an aliquot of the test substance containing the cells into each well;

incubating the test plate;

adding to each well a histochemical reagent, which is capable of generating a chromogenic compound as the result of interacting with a biochemical pathway, if an operative enzyme of that pathway is not inhibited by the antibiotic in that well; and, observing the bacterial cells in each well for the presence of the chromogenic compound.

Another aspect of this invention is a method for determining the susceptibility of bacterial cells to an antibiotic, comprising: providing a test substance containing bacterial cells;

providing a test plate having a plurality of wells, each well comprising a growth medium and a different concentration of an antibiotic, which is known to inhibit an operative enzyme of a bacterial biochemical pathway;

placing an aliquot of the test substance containing the cells into each well; incubating the test plate;

adding to each well a histochemical reagent, which is capable of generating a chromogenic compound as the result of interaction with the biochemical pathway, if the operative enzyme is not inhibited by the concentration of antibiotic in that well; and, observing the bacterial cells in each well for the presence of the chromogenic compound.

DETAILED DESCRIPTION OF THE INVENTION

As used herein, the term "susceptibility" refers to the degree to which a bacterial cell is affected by an antibiotic. That is, the cell may not be affected at all, it may have its growth and proliferation slowed or halted without its being killed or it may be killed. Susceptibility also refers to the degree a population of a bacterial species or strain is affected by an antibiotic. In this case, certain highly susceptible cells of the population may be very sensitive and may be killed by very low concentrations of the antibiotic, other, less sensitive cells may have their growth and proliferation slowed while others may not be affected at all.

As used herein, the term "antibiotic" refers to a naturally-occurring substance produced by a microorganism, such as, without limitation, a fungus or a yeast, the substance being useful in the treatment of infectious disease. Antibiotic also refers to semi-synthetic substances wherein a molecular version produced by a microorganism is subsequently modified to achieve desired properties.

As used herein, "bacterial cells" refers to cells of a particular genus, species or strain of bacteria. In a presently preferred embodiment of this invention, the bacterial cells are of the same strain.

As used herein, a "test substance" refers to a solid or liquid material taken from the body of a patient. The substance can be a body fluid such as, without limitation, serum, plasma, blood, spinal fluid, mucus, nasal discharge, vaginal discharge, ocular discharge, spinal fluid or saliva. Or the substance can be a solid material such as tissue or feces.

As used herein, a "growth medium" refers to a liquid, semisolid or solid substance containing all the essential elements for bacteria to grow such as, without limitation, nutrients, carbon sources, oxygen, salts, metals and the like. Examples of growth media known in the art are, without limitation, Mueller-Hinton medium, Thayer-Martin medium, Conradi-Drigalski medium and Guarnieri's gelatin agar.

As used herein, "contacting" refers to bringing a substance containing bacteria into contact with a growth medium and the chemicals therein such that the bacterial cells proliferate in the absence or, if they are resistant, in the presence of an antibiotic but are killed or inhibited by the antibiotic if they are susceptible. By "inhibited" is meant that the growth and/or the proliferation of the bacteria is slowed or stopped, in the latter case only so long as the antibiotic is present.

As used herein, "incubating" refers to maintaining the physical parameters necessary for growth of the bacteria, for example, without limitation, the temperature of the medium, the atmosphere (air, carbon dioxide, etc.) in which the medium is placed and lighting conditions.

As used herein, an "enzyme" refers to a naturally-occurring proteinaceous macromolecular that catalyzes a specific chemical reaction in a living cell. Enzymes are true catalysts in that they are not consumed in the reactions they catalyze.

A "bacterial biochemical pathway" as used herein, refers to a specific biochemical reaction or series of biochemical reactions that occur within bacterial cells for the purpose of effecting a particular chemical conversion and that are essential to the viability of the cell, that is the ability of the cell to grow and proliferate. A biochemical pathway may be, without limitation, a metabolic pathway, a developmental pathway, a signal-transduction pathway or a genetic regulatory circuit. Specific examples of biochemical pathways include, without limitation, folic acid biosynthesis, methionine biosynthesis, pyrimidine biosynthesis, peptidoglycan and Lipid-A precursor biosynthesis, deoxypyrimidine nucleotide/side metabolism, etc. These and other biochemical pathways are well known in the art.

As used herein, "fixing" refers in one sense to classical fixing, that is, to the rapid killing of tissue elements in cell and their preservation and hardening to retain as nearly as possible the same relationship that they had in the living cell. While there are many ways known in the art to fix a cell, all of which are within the scope of this invention, in one aspect of this invention, fixing is accomplished by contacting cells with acetone, ethanol or a combination thereof. In another sense, "fixing," as used herein, refers to activity short of killing a bacterial cell such as, without limitation, stabilization of the cell, either biochemically; e.g., so that, while the cell's overall viability may be detrimentally affected, certain biochemical processes continue to operate, or physically, as fixing a cell to a surface for testing. In addition, fixing may refer to various forms of histochemical fixing, which are well-known to those skilled in the art. Finally, without limitation, fixing may refer to denaturing of enzymes within a cell.

As used herein, the term "histochemical reagent" refers to a compound or mixture of compounds that interact with a specific biochemical pathway in such a manner that a detectable chromogenic compound is generated, directly as the result of the interaction or indirectly, that is, as the result of a secondary interaction of a product of the first interaction. A histochemical reagent may contain along with the chromogenic compound or precursor thereto, such components as, without limitation, cofactors, enzyme activators and electron acceptors or donors.

By "direct generation" of a chromogenic compound is meant the interaction of a chromogenic compound precursor, which may be colorless or of a first color (for example a dye that is colorless or has a first color in its oxidized form and then is colored or changes to a second color in its reduced form), with a step in the biochemical pathway such as, without limitation, a redox cycle, as the result of which the dye is transformed to a colored or a different color form.

By "indirect generation" of a chromogenic compound is meant that a chromogenic compound precursor is attached to a surrogate substrate for an enzyme of a biochemical pathway. When the surrogate substrate interacts with the enzyme, the precursor molecule is cleaved and only then is capable of combining with another molecule to form a chromogenic compound. Indirect generation can also refer to a chromogenic compound precursor that is capable of interacting with a product of an active biochemical pathway to form a chromogenic compound.

By "interacts" or "interaction" with a biochemical pathway is meant that a compound is converted by a chemical or physical process in the biochemical pathway to a different form. The different form may be, for example, without limitation, a different chemical species created by an enzyme-catalyzed reaction of the compound such as, without limitation, cleavage, carboxylation, hydrolysis, etc., a different oxidation state as the result of electron exchange in a redox cycle of the biochemical pathway or a form in which the compound is covalently bonded to a natural product of the biochemical pathway.

Depending on the nature of the histochemical reagent, it may be necessary to add the components of the reagent to the test substrate all at once or in a predetermined sequence to generate the chromogenic compound.

As used herein, the phrase "operative enzyme" refers to an enzyme the catalytic activity of which is essential to the reaction or sequence of reactions comprising a targeted biochemical pathway, that is, if the enzyme is inhibited the biochemical pathway ceases to operate.

As used herein, "inhibit" or "inhibiting" an operative enzyme refers to interfering with the ability of the enzyme to conduct its normal catalytic activity.

As used herein, a "chromogenic compound" refers to a compound that can be detected as the result of its ability to absorb or emit light. The absorption of light may result in the generation of a color or a change in color in the visible region, that is, a color or color change visible to the naked eye or using an instrument such as, without limitation, a light microscope or a laser scanner. In addition, the absorption of light may occur in the non-visible region of the spectrum, e.g., the ultraviolet or infrared regions of the spectrum, in which case the absorption would be detected instrumentally using a spectrophotometer. Light emission includes fluorescence, wherein a compound, while absorbing light a one wavelength emits light of a different wavelength or phosphorescence where a compound absorbs light at one wavelength and emits light of a different wavelength for a period of time after the incident light is turned off.

By "observing" the bacterial cells is meant that the cells are simply looked at with the naked eye to see of any color has developed in the cells. In some cases front or back illumination of the cells may facilitate the observation. Observing also means looking at the cells using an instrument such as a light microscope, a laser scanner or a UV spectrophotometer.

A "patient" refers to any life form that is susceptible to bacterial infections such as fish, reptiles, birds and mammals. In particular, mammals, such as dogs, cats, horses, cattle, sheep and the like are patients within the context of this invention. In a presently preferred embodiment of this invention, the patient is a human being.

Most antibiotics kill or inhibit bacteria by interfering with the activity of one or more enzymes necessary for the functioning of the cell. Examples of some common antibiotics and the enzymes they inhibit include: beta-lactams, which inhibit the activity of transpeptdases; Gentamicin, which interferes with peptidyl transferase activity; Sulfamethoxazole, which inhibits tetrahydropteroic acid synthetase activity; and Trimethoprim, which interferes with dihydrofolate reductase activity. A more complete listing of antibiotic classes and enzymes they inhibit may be found in Fish, et al., supra, which is incorporated, including any drawings, as if fully set forth herein.

Interference with the activity of an enzyme by an antibiotic will occur immediately upon contact of the antibiotic with the target enzyme. This interference will, in most cases, be detectable long before overt bacteristatic or bactericidal effects are observed. Thus, an aspect of this invention is a method for early detection of antibiotic susceptibility using a histochemical reagent that generates a detectable chromogenic compound as the result of interaction with a biochemical pathway in a cell, which pathway is selected because an enzyme operative in that pathway is the target of the antibiotic. In cells that are resistant to a particular antibiotic, the enzyme will not be inhibited, the pathway will not cease to operate and the histochemical reagent will interact with the pathway to generate a chromogenic compound. However, in a susceptible cell, the enzyme will be inhibited by the antibiotic, the biochemical pathway will cease to operate, the histochemical reagent will not be able to interact with the pathway and no chromogenic compound will be generated.

It is necessary to the method of the present invention that the specific mode of action of a particular antibiotic, that is, the biochemical pathway and the enzyme in that pathway that the antibiotic inhibits, be known. Fortunately, for virtually all antibiotics of clinical importance, such is the case. Based on this knowledge and the disclosures herein, a histochemical reagent capable of interaction with the particular pathway, and thereby generating a chromogenic compound, can be prepared. For instance, without limitation, a histochemical reagent may be prepared that contains a compound which mimics the natural substrate for the target enzyme so that the enzyme catalyzes a reaction of the compound which results in the generation of a chromogenic compound. Or a histochemical reagent may be prepared that contains a compound that is colorless (or of a first color) in one oxidation state and colored (or of a different color) in another oxidation state. The compound could then interact with a redox cycle in the biochemical pathway, as the result of which its oxidation state, and therefore its color, would be changed. A still further example would be a histochemical reagent containing a compound which can react with the product of an enzymatic reaction in the biochemical pathway, the product of the reaction being a chromogenic compound. Other such histochemical reagents will be apparent to those skilled in the art based on the disclosures herein.

Once a histochemical reagent specific for an enzyme-catalyzed biochemical pathway has been prepared, the susceptibility of a bacterial strain can be rapidly determined by contacting bacteria cells with an antibiotic followed a brief incubation and then contact with the histochemical reagent. If the bacterial cells are resistant to the antibiotic, the chromogenic compound will be produced and can be detected long before it becomes apparent that the cells are being killed or their growth inhibited which would require culturing the cells.

The method described herein can, of course, be applied to determine the susceptibility of bacterial cells to one antibiotic at a time. However, it is a preferred embodiment of this invention that a plurality of antibiotics are provided in a format in which the susceptibility of bacterial cells to all of the antibiotics can be determined simultaneously. For example, without limitation, a series of antibiotics, or different concentration of an antibiotic, which inhibit the same enzyme in the same biochemical pathway, are placed in each well of a standard 96-well titer plate along with a growth medium. An aliquot of a bacteria-containing substance is placed in each well and the plate is incubated. After incubation, a histochemical reagent is added to each well. Each well is then observed under a microscope to determine to which antibiotic the bacteria are resistant or susceptible to, as evidenced by the presence or absence of a chromogenic compound in the bacterial cells in those wells.

EXAMPLES

1. General Procedure

An aliquot of a substance which contains the bacteria of interest is mixed with a growth medium containing an antibiotic. Any substance that contains bacteria may be used but, in a preferred embodiment of this invention, the substance is obtained from a patient, usually in the form of a body fluid. Another aliquot of the substance is mixed with the same growth medium but which does not contain any antibiotic, this aliquot being a control sample. Both aliquots are then incubated for about 10 minutes to about 2 hours, preferably about 30 minutes to about 1.5 hours. At this point, the aliquots may optionally be treated to remove any endogenous materials that might interact with the histochemical reagent and give a false positive or false negative result. The aliquots may also optionally be treated with a fixative to fix the cells prior to addition of the histochemical reagent. Finally, the histochemical reagent is added to the aliquots. The bacterial cells are then inspected for the presence of a chromogenic compound, that is, for the presence of color This can often be observed by the naked eye but instrumental means, such as, without limitation, a light microscope, a laser scanner or a UV spectrophotometer may also be used. A chromogenic compound should be generated in the control (the aliquot with no added antibiotic) since there was no antibiotic present to interfere with the biochemical pathway that the histochemical agent was designed to interact with. The cells in the aliquot containing the antibiotic will likewise be stained if the bacteria are resistant to the antibiotic. On the other hand, cells will not be stained if the bacteria are susceptible to the antibiotic.

2. β-Lactam Antibiotic Susceptibility

The β-lactam antibiotics function by inhibiting the enzymatic activity of D-ala-D-ala transpeptidase and D-ala-D-ala carboxypeptidase, also known as penicillin binding protein or PBP. The natural substrate for these enzymes is a pentapeptide having the sequence NacMur-L-ala-D-gln-X(—NH$_2$)-D-ala-D-ala. X is either L-lysine (L-lys) or m-diaminopimelic acid. It is known that the D-ala-D-ala carboxypeptidase cleaves the pentapeptide at the D-ala-D-ala sequence. Thus, a synthetic substrate which has sufficient similarity to the natural substrate to bind to the active site of the enzyme but which contains a chromogenic compound or compound precursor attached to the D-ala-D-ala sequence should be cleaved by the enzyme, thus releasing the chromogentic compound. Possible pentapeptide mimics include the following:

D-ala-D-ala-1-naphthylamide monohydrate
D-ala-D-ala-γ-(4-methoxy-β-naphthylamide)
L-lys-D-ala-D-ala-1-naphthylamide monohydrate
L-lys-D-ala-D-ala-γ(4-methoxy-β-naphthylamide)
D-gln-L-lys-D-ala-D-ala-1-naphthylamide monohydrate
D-gln-L-lys-D-ala-D-ala-γ-(4-methoxy-β-naphthylamide)
L-ala-D-gln-L-lys-D-ala-D-ala-1-naphthylamide monohydrate
L-ala-D-gln-L-lys-D-ala-D-ala-γ-(4-methoxy-β-naphthylamide)

When separated from the peptide chain by the enzyme, the naphthylamide or 4-methoxy-γ-naphthylamide can react with a dye precursor to generate a detectable chromogenic compound. For instance, Garnet GBC or Fast Garnet GBC will give a colored product with 1-naphthylamide monohydrate and Fast Blue B or Fast Blue BB will give a colored product with 4-methoxy-β-naphthylamide.

2. Trimethoprim Susceptibility

Timethoprim acts by inhibiting the activity of dihydrofolate reductase which is a step in the biochemical pathway leading for folic acid synthesis. A necessary cofactor for the enzymatic reaction is NADP or NADPH. Magnesium chloride is an activator for the enzyme. Thus, in a test to determine if a histochemical reaction could be used to determine susceptibility of a bacterial strain to trimethylprim, E. coli ATCC 25922 cells were washed with pH6 phosphate buffer (PB) solution or with pH6 PB containing hydrogen peroxide to remove endogenous substrates and cofactors present in the cells that might give a false result, that is, a stained bacterial cell indicating resistance when, in fact, the actual biochemical pathway was inhibited by the antibiotic. The cells were then put into 0.01 M pH6 PB and contacted with a mixture of three different concentrations of trimethoprim, 0.003, 0.03 and 0.3 mM, the oxidized form of tetranitro blue tetrazolium salt (TNBT), which in its oxidized state is colorless, magnesium chloride and sodium azide (a respiratory chain blocker). After 30 minutes, dihydrofolic acid (0.03 mM) and NADP (0.08 mM) were added and the cells were left for another 30 minutes. When viewed under a microscope, cells treated with 0.003 mM trimethoprim were heavily stained, those treated with 0.03 mM were lightly stained and those treated with 0.3 mM were completely unstained. This indicated that the reaction catalyzed by dihydrofolate reductase in the cells was completely inhibited by 0.3 mM of trimethoprim, partially inhibited by 0.03 mM and unaffected by 0.003 mM trimethoprim.

CONCLUSION

Thus, it will be appreciated that the present invention provides a method for the rapid determination of bacterial susceptibility to antibiotics, which should permit more specific initial treatment of bacterial infections.

Other embodiments of this invention are set forth in the following claims.

What is claimed:

1. A method for determining susceptibility of bacterial cells to an antibiotic comprising:

providing a test substance containing bacterial cells, the susceptibility of which to an antibiotic is sought;

contacting the test substance with a growth medium containing the antibiotic, which is known to inhibit an operative enzyme of a bacterial biochemical pathway, to form a test substrate;

incubating the test substrate;

adding to the test substrate a histochemical reagent capable of generating a chromogenic compound as the result of interaction with the operative enzyme of the biochemical pathway; and, observing the bacterial cells in the test substrate for the presence of the chromogenic compound, wherein:
if the chromogenic compound is observed, then the operative enzyme is not inhibited and the bacteria are not susceptible to the antibiotic whereas, if the chromogenic compound is not observed, then the bacteria are susceptible to the antibiotic.

2. The method of claim 1, further comprising:

contacting an aliquot of the test substance containing the bacterial cells with growth medium not containing the antibiotic to form a control substrate;

incubating the control substrate;

adding the histochemical reagent to the control substrate; and, observing the bacterial cells in the control substrate for the presence of the chromogenic compound.

3. The method of claim 1, wherein the bacterial cells are selected from the group consisting of Pseudomonas, Eschericia, Streptococcus, Staphlococcus, Enterococcus, Enterobacteriaceae, Mycobacteria, Klebsiella and Haemophilis.

4. The method of claim 1, wherein the operative enzyme is selected from the group consisting of transpeptidase, carboxypeptidase, tetrahydropteroic acid synthetase and dihydrofolate reductase.

5. The method of claim 1, wherein the antibiotic is selected from the group consisting of a β-lactam, a tetracycline, an aminoglycoside, a sulfonamide, a macrolide, a fluoroquinolone and trimethoprim antibiotic.

6. The method of claim 1, wherein the antibiotic is selected from the group consisting of ampicillin, cefazolin, cephalothin, ceftazidime, gentamycin, mezlocillin, oxacillin, penicillin, piperacillin, ticarcillin and trimethoprim.

7. The method of claim 1, wherein the test substrate, and control substrate if used, are incubated from about 1 to about 120 minutes.

8. The method of claim 7, wherein the test substrate, and the control substrate if used, are incubated from about 30 to about 90 minutes.

9. The method of claim 7, wherein the test substrate, and the control substrate if used, are incubated from about 10 to about 40 minutes.

10. The method of claim 1 wherein the test substance comprises a body fluid.

11. The method of claim 10, wherein the body fluid is selected from the group consisting of serum, plasma, spinal fluid, phlegm, saliva, nasal discharge, ocular discharge and pus.

12. The method of claim 1, wherein the test substance is selected from group consisting of tissue and feces.

13. The method of claim 1, wherein the chromogenic compound is observable by the naked eye.

14. The method of claim 1, wherein the chromogenic compound is observed using instrumental means.

15. The method of claim 14, wherein the instrumental means comprises a light microscope, a UV spectrophotometer or a laser scanner.

16. The method of claim 1, wherein:

the antibiotic is trimethoprim;

the enzyme-catalyzed biochemical pathway is a folic acid synthesis pathway;

the test substrate is washed with pH6 phosphate buffer prior to contact with the histochemical reagent; and, the histochemical reagent comprises tetra nitro blue tetrazolium (TNBT), magnesium chloride, sodium azide, nicotinamide adenine diphosphate (NADP) and dihydrofolic acid.

17. A method for determining the susceptibility of bacterial cells to a plurality of antibiotics, comprising:

providing a test substance containing bacterial cells;

providing a test plate having a plurality of wells, each well comprising a growth medium and a different antibiotic, wherein each antibiotic is known to inhibit an operative enzyme of a bacterial biochemical pathway;

placing an aliquot of the test substance containing the cells into each well;

incubating the test plate;

adding to each well a histochemical reagent, which is capable of generating a chromogenic compound as the result of interacting with the operative enzyme of the biochemical pathway; and, observing the bacterial cells in each well for the presence of the chromogenic compound, wherein:
in any well in which the chromogenic compound is observed, the operative enzyme is not inhibited and the bacteria are not susceptible to the antibiotic in that well whereas, in any well in which the chromogenic compound is not observed, the bacteria are susceptible to the antibiotic in that well.

18. A method for determining the susceptibility of bacterial cells to an antibiotic, comprising:

providing a test substance containing bacterial cells;

providing a test plate having a plurality of wells, each well comprising a growth medium and a different concentration of an antibiotic, which is known to inhibit an operative enzyme of a bacterial biochemical pathway;

placing an aliquot of the test substance containing the cells into each well;

incubating the test plate;

adding to each well a histochemical reagent, which is capable of generating a chromogenic compound as the result of interaction with the operative enzyme of the biochemical pathway; and, observing the bacterial cells in each well for the presence of the chromogenic compound, wherein:
in any well in which the chromogenic compound is observed, the operative enzyme is not inhibited and the bacteria are not susceptible to the antibiotic at the concentration in that well whereas, in any well in which the chromogenic compound is not observed, the bacteria are susceptible to the antibiotic at the concentration in that well.

* * * * *